(12) United States Patent
Kääriäinen et al.

(10) Patent No.: US 7,989,192 B2
(45) Date of Patent: Aug. 2, 2011

(54) MODIFIED BETA-LACTAMASE AND METHOD FOR ITS PREPARATION

(75) Inventors: Susanna Kääriäinen, Espoo (FI); Nina Wickstrand, Helsinki (FI); Pertti Koski, Helsinki (FI)

(73) Assignee: IPSAT Therapies Oy, Helsinki (FI)

( * ) Notice: Subject to any disclaimer, the term of this patent is extended or adjusted under 35 U.S.C. 154(b) by 0 days.

(21) Appl. No.: 12/304,874

(22) PCT Filed: Jun. 19, 2007

(86) PCT No.: PCT/FI2007/050372
§ 371 (c)(1),
(2), (4) Date: Dec. 15, 2008

(87) PCT Pub. No.: WO2007/147945
PCT Pub. Date: Dec. 27, 2007

(65) Prior Publication Data
US 2009/0181004 A1    Jul. 16, 2009

(30) Foreign Application Priority Data

Jun. 21, 2006  (FI) ..................... 20065431

(51) Int. Cl.
*C12N 9/14*      (2006.01)
*A61K 38/46*     (2006.01)
*C07H 21/04*     (2006.01)
(52) U.S. Cl. ...................... 435/195; 424/94.6; 536/23.2
(58) Field of Classification Search .................. 435/195; 424/94.6; 536/23.2
See application file for complete search history.

(56) References Cited

FOREIGN PATENT DOCUMENTS

| WO | 9313795 A1 | 7/1993 |
|---|---|---|
| WO | 03040352 A1 | 5/2003 |
| WO | 2004016248 A2 | 2/2004 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Pluckthun et al., The consequence of of stepwise deletions from the signal-processing site of beta-lactamase. J. Biol.Chem., 1987, vol. 262 (9): 3951-3957.*
Sen et al., Developments in directed evolution for improving enzyme functions. Appl. Biochem. Biotechnol., 2007, vol. 143: 212-223.*
Wishart et al., A single mutation converts a novel phosphotyrosine binding domain into a dual-specificity phosphatase. J. Biol. Chem., 1995, vol. 270(45): 26782-26785.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Supplementary EP Search Report relating to Corresponding EP 07765926.6, Oct. 24, 2007.
Garau et al., "Update of the Standard Numbering Scheme for Class B β-Lactamases," Guest Commentary Antimicrobial Agents and Chemotherapy, Jul. 2004, pp. 2347-2349, vol. 48, No. 7.
Crawford, et al., "Over-expression, purification, and characterization of metallo-β-lactamase ImiS from Aeromonas veronii bv. sobria," Protein Expression and Purification 36 (2004) 272-279.
A. Carfi, S. Pares, E. Duee, M. Galleni, C. Duez, J.M. Frere and O. Dideberg. The 3-D structure of a zinc metallo-Beta-lactamase from *Bacillus cereus* reveals a new type of protein fold, The EMBO Journal, 1995, vol. 14 No. 20: 4914-4921.
Jaana Harmoinen, Silja Mentula, Matti Heikkila, Michel Van Der Rest, Paivi J. Rajala-Schultz, Curtis J. Donskey, Rafael Frias, Pertti Koski, Nina Wickstrand, Hannele Jousimies-Somer, Elias Westermarck, and Kai Lindevall. Orally Administered Targeted Recombinant Beta-Lactamase Prevents Ampicillin-Induced Selective Pressure on the Gut Microbiota: a Novel Approach to Reducing Antimicrobial Resistance. Antimicrobial Agents and Chemotherapy, Jan. 2004, vol. 48 No. 1: 75-79.
Karen Bush. Metallo-Beta-Lactamases: A Class Apart. Clinical Infectious Diseases, 1998; 27(Suppl 1):S48-53.
Nestor O. Concha, Cheryl A. Janson, Pam Rowling, Stewart Pearson, Christy A. Cheever, Brian P. Clarke, Ceri Lewis, Moreno Galleni, Jean-Marie Frere, David J. Payne, John H. Bateson, and Sherin S. Abdel-Meguid. Crystal Structure of the IMP-1 Metallo Beta-Lactamase from *Pseudomonas aeruginosa* and Its Complex with a Mercaptocarboxylate Inhibitor: Binding Determinants of a Potent, Broad-Spectrum Inhibitor. Biochemistry (2000) 39(15): 4288-4298.
Gianpiero Garau, Carine Bebrone, Christine Anne, Moreno Galleni, Jean-Marie Frere and Otto Dideberg. A Metallo-Beta-lactamase Enzyme in Action: Crystal Structures of the Monozinc Carbapenemase CphA and its Complex with Biapenem. J. Mol. Biol. (2005) 345, 785-795.
Silja Mentula, Jaana Harmoinen, Pertti Koski, Elias Westermarck, Merja Rautio, Pentti Huovinen, and Eija Kononen. Inhibition of ampicillin-induced emergence of resistance in intestinal coliforms by targeted recombinant Beta-lactamase. International Journal of Antimicrobial Agents, (2004)24:555-561.

(Continued)

*Primary Examiner* — Ganapathirama Raghu
(74) *Attorney, Agent, or Firm* — Banner & Witcoff, Ltd.

(57) ABSTRACT

The invention relates to targeted post translational modification of metallo-beta-lactamase by truncation and insertion of a dipeptide at the amino terminal end to reduce amino terminal heterogeneity in a recombinant DNA production system. A protein K-T-E-ΔBL is expressed, and modified by host proteases to E-ΔBL. Appropriate nucleotide molecules, vectors and hosts are also described. E-ΔBL is useful in a pharmaceutical composition for treating antibiotic induced adverse effects in the intestine of patients treated with beta-lactam antibiotics.

12 Claims, 3 Drawing Sheets

OTHER PUBLICATIONS

Usha Stiefel, Jaana Harmoinen, Pertti Koski, Susanna Kaariainen, Nina Wickstrand, Kai Lindevall, Nicole J. Pultz, Robert A. Bonomo, Marion S. Helfand and Curtis J. Donskey. Orally Administered Recombinant Metallo-Beta-Lactamase Preserves Colonization Resistance of Piperacillin-Tazobactam-Treated Mice. Antimicrobial Agents and Chemotherapy, (Dec. 2005) vol. 49 No. 12: 5190-5191.

Jan Walther-Rasmussen, Anders H. Johnsen and Niels Hoiby. Terminal truncations in Amp C Beta-lactamase from a clinical isolate of *Pseudomonas aeruginosa*. Eur. J. Biochem.(1999) 263: 478-485.

Andrea Carfi, Emile Duee, Raquel Paul-Soto, Moreno Galleni, Jean-Marie Frere and Otto Dideberg. X-ray Structure of the Zn11 Beta-Lactamase from *Bacteroides fragilis* in an Orthorhombic Crystal Form. Acta. Cryst. (1998) D54: 47-57.

Stephen F. Altschul, Thomas L. Madden, Alejandro A. Schaffer, Jinghui Zhang, Zheng Zhang, Webb Miller and David J. Lipman. Gapped BLAST and PSI-BLAST: a new generation of protein database search programs. Nucleic Acids Research, 1997, vol. 25, No. 17: 3389-3402.

Moreno Galleni, Josette Lamotte-Brasseur, Gian Maria Rossolini, Jim Spencer, Otto Dideberg, Jean-Marie Frere and the Metallo-Beta-Lactamase Working Group. Standard Numbering Scheme for Class B Beta-Lactamases. Antimicrobial Agents and Chemotherapy, Mar. 2001, vol. 45, No. 3, pp. 660-663.

Usha Stiefel, Nicole J. Pultz, Jaana Harmoinen, Pertti Koski, Kai Lindevall, Marion S. Helfand and Curtis J. Donskey. Oral Administration of Beta-Lactamase Preserves Colonization Resistance of Piperacillin-Treated Mice. The Journal of Infectious Diseases (2003) 188:1605-1609.

R.P. Ambler, A.F.W. Coulson, J.-M. Frere, J.-M. Ghuysen, B. Joris, M. Forsman, R.C. Levesque, G. Tiraby, and S.G. Waley. A standard numbering scheme for the Class A Beta-lactamases. Biochem. J. (1991) 276:269-272.

Andrea Carfi, Emile Duee, Moreno Galleni, Jean-Marie Frere and Otto Dideberg. 1.85 A Resolution Structure of the Zinc II Beta-Lactamase from *Bacillus cereus*. Acta Cryst. (1998) D54: 313-323.

Gianpiero Garau, Isabel Garcia-Saez, Carine Bebrone, Christine Anne, Paola Mercuri, Moreno Galleni, Jean-Marie Frere and Otto Dideberg. Update of the Standard Numbering Scheme for Class B Beta-Lactamases. Antimicrobial Agents and Chemotherapy, Jul. 2004, vol. 48 No. 7: 2347-2349.

J. Marmur. A Procedure for the Isolation of Deoxyribonucleic Acid from Micro-organisms. J. Mol. Biol. (1961) 3: 208-218.

Alan M. Simm, Catherine S. Higgins, Anne L. Carenbauer, Michael W. Crowder, John H. Bateson, Peter M. Bennett, Anthony R. Clarke, Stephen E. Halford and Timothy R. Walsh. Characterization of Monomeric L1 Metallo-Beta-lactamase and the Role of the N-terminal Extension in Negative Cooperativity and Antibiotic Hydrolysis. The Journal of Biological Chemistry (Jul. 2002) vol. 277 No. 27: 24744-24752.

Timothy R. Walsh, Mark A. Toleman, Laurent Poirel and Patrice Nordmann. Metallo-Beta-Lactamases: the Quiet before the Storm? Clinical Microbiology Reviews (Apr. 2005) vol. 18 No. 2: 306-325.

Finnish Patent Search Report from Finnish Patent Office for FI 20065431, Oct. 24, 2007.

* cited by examiner

Figure 1

```
  1 atgaaaaagaatacattattaaaattaggggtatgtgttagttta
    M  K  K  N  T  L  L  K  L  G  V  C  V  S  L
    -30
 46 ctaggaataactcaatttgttagtacaatttcttctgtgaaagca
    L  G  I  T  Q  F  V  S  T  I  S  S  V  K  A
                                              -1
 91 gaacaaaagctagagcaaatagtaatcaaaaatgagacgggaacc
    E  Q  K  L  E  Q  I  V  I  K  N  E  T  G  T
    +1
136 atttcaatatctcagttaaacaagaatgtatgggttcatacggag
    I  S  I  S  Q  L  N  K  N  V  W  V  H  T  E 181 ttaggttattttaatggagaagcagttccttcgaacggtctagtt
    L  G  Y  F  N  G  E  A  V  P  S  N  G  L  V 226 cttaatacttctaaagggctagtacttgttgattcttcttgggat
    L  N  T  S  K  G  L  V  L  V  D  S  S  W  D 271 aacaaattaacgaaggaactaatagaaatggtagaaaagaaattt
    N  K  L  T  K  E  L  I  E  M  V  E  K  K  F 316 cagaagcgcgtaacggatgtcattattacacatgcgcacgctgat
    Q  K  R  V  T  D  V  I  I  T  H  A  H  A  D 361 cgaattggcggaataacagcgttgaaagaaagaggcattaaagcg
    R  I  G  G  I  T  A  L  K  E  R  G  I  K  A 406 catagtacagcattaaccgcagaactagcaaagaacagtggatat
    H  S  T  A  L  T  A  E  L  A  K  N  S  G  Y 451 gaagagccgcttggagatttacaaacaattacgagttaaagttt
    E  E  P  L  G  D  L  Q  T  I  T  S  L  K  F 496 ggcaatacaaaagtagaaacgttctatccagggaaaggacataca
    G  N  T  K  V  E  T  F  Y  P  G  K  G  H  T 541 gaagataatattgttgtttggttgccacaatatcaaattttagct
    E  D  N  I  V  V  W  L  P  Q  Y  Q  I  L  A 586 ggaggctgtttagtaaaatctgcggaagctaaagatttaggaaat
    G  G  C  L  V  K  S  A  E  A  K  D  L  G  N 631 gttgcggatgcgtatgtaaatgaatggtctacatcgattgagaat
    V  A  D  A  Y  V  N  E  W  S  T  S  I  E  N 676 gtgctgaagcgatatggaaatataaattcggtagtacctggtcat
    V  L  K  R  Y  G  N  I  N  S  V  V  P  G  H 721 ggagaagtaggagacaagggattacttttacatacattggattta
    G  E  V  G  D  K  G  L  L  L  H  T  L  D  L
766 ttaaaataa 774
    L  K  *
```

Figure 2

```
  1 atgattcaaaaacgaaagcggacagtttcgttcagacttgtgctt
    M  I  Q  K  R  K  R  T  V  S  F  R  L  V  L
    -31
 46 atgtgcacgctgttatttgtcagtttgccgattacaaaaacatca
    M  C  T  L  L  F  V  S  L  P  I  T  K  T  S 91 gcgcaagcttccgaacaaaagctagagcaaatagtaatcaaaaat
    A  Q  A  S  E  Q  K  L  E  Q  I  V  I  K  N
    -1 +1
136 gagacgggaaccatttcaatatctcagttaaacaagaatgtatgg
    E  T  G  T  I  S  I  S  Q  L  N  K  N  V  W 181 gttcatacggagttaggttattttaatggagaagcagttccttcg
    V  H  T  E  L  G  Y  F  N  G  E  A  V  P  S 226 aacggtctagttcttaatacttctaaagggctagtacttgttgat
    N  G  L  V  L  N  T  S  K  G  L  V  L  V  D 271 tcttcttgggataacaaattaacgaaggaactaatagaaatggta
    S  S  W  D  N  K  L  T  K  E  L  I  E  M  V 316 gaaaagaaatttcagaagcgcgtaacggatgtcattattacacat
    E  K  K  F  Q  K  R  V  T  D  V  I  I  T  H 361 gcgcacgctgatcgaattggcggaataacagcgttgaaagaaaga
    A  H  A  D  R  I  G  G  I  T  A  L  K  E  R 406 ggcattaaagcgcatagtacagcattaaccgcagaactagcaaag
    G  I  K  A  H  S  T  A  L  T  A  E  L  A  K 451 aacagtggatatgaagagccgcttggagatttacaaacaattacg
    N  S  G  Y  E  E  P  L  G  D  L  Q  T  I  T 496 agtttaaagtttggcaatacaaaagtagaaacgttctatccaggg
    S  L  K  F  G  N  T  K  V  E  T  F  Y  P  G 541 aaaggacatacagaagataatattgttgtttggttgccacaatat
    K  G  H  T  E  D  N  I  V  V  W  L  P  Q  Y 586 caaattttagctggaggctgtttagtaaaatctgcggaagctaaa
    Q  I  L  A  G  G  C  L  V  K  S  A  E  A  K 631 gatttaggaaatgttgcggatgcgtatgtaaatgaatggtctaca
    D  L  G  N  V  A  D  A  Y  V  N  E  W  S  T 676 tcgattgagaatgtgctgaagcgatatggaaatataaattcggta
    S  I  E  N  V  L  K  R  Y  G  N  I  N  S  V 721 gtacctggtcatggagaagtaggagacaagggattacttttacat
    V  P  G  H  G  E  V  G  D  K  G  L  L  L  H 766 acattggatttattaaaataa 786
    T  L  D  L  L  K  *
```

Figure 3

```
atgattcaaaaacgaaagcggacagtttcgttcagacttgtgcttatg
 M  I  Q  K  R  K  R  T  V  S  F  R  L  V  L  M tgcacgctgttatttgtcagtttgccgattacaaaaacatcagcg
 C  T  L  L  F  V  S  L  P  I  T  K  T  S  A
                                              -1
caagcttccaaaacagagacgggaaccatttcaatatctcagttaaacaagaatgtatgg
 Q  A  S  K  T  E  T  G  T  I  S  I  S  Q  L  N  K  N  V  W
+1
gttcatacggagttaggttattttaatggagaagcagttccttcgaacggtctagttctt
 V  H  T  E  L  G  Y  F  N  G  E  A  V  P  S  N  G  L  V  L aatacttctaaagggctagtacttgttgattcttcttgggataacaaattaacgaaggaa
 N  T  S  K  G  L  V  L  V  D  S  S  W  D  N  K  L  T  K  E ctaatagaaatggtagaaaagaaatttcagaagcgcgtaacggatgtcattattacacat
 L  I  E  M  V  E  K  K  F  Q  K  R  V  T  D  V  I  I  T  H gcgcacgctgatcgaattggcggaataacagcgttgaaagaaagaggcattaaagcgcat
 A  H  A  D  R  I  G  G  I  T  A  L  K  E  R  G  I  K  A  H agtacagcattaaccgcagaactagcaaagaacagtggatatgaagagccgcttggagat
 S  T  A  L  T  A  E  L  A  K  N  S  G  Y  E  E  P  L  G  D ttacaaacaattacgagtttaaagtttggcaatacaaaagtagaaacgttctatccaggg
 L  Q  T  I  T  S  L  K  F  G  N  T  K  V  E  T  F  Y  P  G aaaggacatacagaagataatattgttgtttggttgccacaatatcaaattttagctgga
 K  G  H  T  E  D  N  I  V  V  W  L  P  Q  Y  Q  I  L  A  G ggctgtttagtaaaatctgcggaagctaaagatttaggaaatgttgcggatgcgtatgta
 G  C  L  V  K  S  A  E  A  K  D  L  G  N  V  A  D  A  Y  V aatgaatggtctacatcgattgagaatgtgctgaagcgatatggaaatataaattcggta
 N  E  W  S  T  S  I  E  N  V  L  K  R  Y  G  N  I  N  S  V gtacctggtcatggagaagtaggagacaagggattacttttacatacattggatttatta
 V  P  G  H  G  E  V  G  D  K  G  L  L  L  H  T  L  D  L  L aaataa
 K  *
```

MODIFIED BETA-LACTAMASE AND METHOD FOR ITS PREPARATION

RELATED APPLICATIONS

This application claims priority from PCT application number PCT/FI2007/050372, filed Jun. 19, 2007; which claims priority from Finnish patent application number 20065431, filed Jun. 21, 2006; each of which is hereby incorporated herein by reference in its entirety for all purposes.

FIELD OF THE INVENTION

Various antibiotics are used in the treatment of bacterial infections. However, the antibiotics do not only attack pathogens, but they also affect the normal bacterial flora, leading to adverse side effects e.g. in the patient's intestine. These side effects can be reduced by administering enzymes capable of degrading residual antibiotic in the intestine. The present invention relates to modified metallo-beta-lactamases that are useful in treating and preventing adverse effects of antibiotics having a beta-lactam ring, or in the preparation of such enzymes. The invention is also directed to a method for preparing the modified beta-lactamases as well as to nucleotide molecules, vectors and host cells useful therein.

BACKGROUND OF THE INVENTION

Beta-lactamase enzymes represent a major mechanism of resistance among bacteria to beta-lactam antibiotics, which include penicillins, cephalosporins and carbapenems. These enzymes catalyse the irreversible hydrolysis of the amide bond of the beta-lactam ring to create ineffective antimicrobial agents. On the basis of molecular structure classification and catalytic mechanisms the beta-lactamases can be divided into four classes: A, B, C, and D. Classes A, C and D are serine enzymes and comprise the majority of the beta-lactamases (Ambler, 1980). These enzymes generally inactivate penicillins or cephalosporins and often show a preference for one of these two antibiotics.

Class B beta-lactamases are metallo-enzymes that require one or two zinc ions as a cofactor for enzyme activity. The metallo-beta-lactamases constitute group 3 in the Bush-Jacoby-Madeiros functional classification (Bush, 1998). This schema is primarily based on substrate profiles, their sensitivity to EDTA and their resistance to serine beta-lactamase inhibitors. Based on structural similarities in the region that coordinates zinc binding, metallo-beta-lactamases can be divided into three subgroups, B1, B2, and B3 (Galleni et al., 2001). Subgroup B1 possesses three histidines and one cysteine as the key zinc coordinating residues. Crystallographic structures have been described for many subgroup B1 enzymes such as BcII of *Bacillus cereus* (Carfi et al, 1995 and 1998a), CcrA of *Bacteroides fragilis* and (Carfi et al., 1998b) and IMP-1 of *Pseudomonas aeruginosa* (Concha et al., 2000). Correspondingly, subgroup B2 lactamases have an arginine residue, instead of histidine, at the first position of the principal zinc binding motif, NXHXD (SEQ ID NO:39). Recently, the first crystal structure of a subgroup B2 enzyme (CphA) has been solved by Garau et al. (2005). Subgroup B3 contains enzymes with multimeric structure (Walsh et al., 2005).

Metallo-beta-lactamases show a broad spectrum substrate profile including penicillins and cephalosporins, and they are resistant to the action of common conventional serine beta-lactamase inhibitors such as clavulanic acid sulbactam and tazobactam. Furthermore, unlike most of the serine beta-lactamases, metallo-beta-lactamases have the capability to hydrolyze carbapenems such as meropenem and imipenem. Various numbers of bacteria are known to produce metallo-beta-lactamases. They are commonly expressed among the *Enterobacteriae* ogenus (including *Serratia marcescens, Klebsiella pneumoniae, Citrobacter freudii, Shigella flexneri*), *Pseudomonas aeruginosa, Stenobacterium maltophila, Acinetobacter* genus, *Bacteroides fragilis, Bacillus cereus, Flavobacteruim odoratum*, and *Bacteroides fragilis* (Walsh et al., 2005).

Beta-lactamases can be utilized as pharmaceutical proteins to inactivate unabsorbed beta-lactams in the gastro intestinal tract in order to prevent the beta-lactam induced adverse effects including alterations in intestinal normal microbiota and the overgrowth of beta-lactam resistant bacteria (WO93/13795, WO2004/016248). For efficient beta-lactamase therapy in the small intestinal tract the enzyme should be resistant to the action of intestinal proteases in the presence of bile acids and preserve high enzymatic activity at a wide range of pH (5.5-7.5).

The feasibility of targeted enzyme therapy in canine and mouse models was demonstrated by employing a *Bacillus licheniformis* serine beta-lactamase during parenteral ampicillin medication (Harmoinen et al., 2004, Mentula et al., 2004, Stiefel et al., 2003). However, the substrate profile of this enzyme essentially limits its use as a drug substance since it has poor capacity to hydrolyze cephalosporins, carbapenems or penicillins in the presence of beta-lactamase inhibitors. Consequently, a new protease resistant beta-lactamase enzyme with broad beta-lactam spectrum is indispensable to extend the use of beta-lactamase therapy among hospitalized patients under intravenous medication with various beta-lactams.

Metallo-beta-lactamases are known to inactivate various types of beta-lactams and they are resistant to inhibitors of serine beta-lactamases. *Bacillus cereus* strains are known to produce metallo-beta-lactamase that belongs to group B1. A semi purified recombinantly produced metallo-beta-lactamase sample of a clinical *Bacillus cereus* 98ME1552 isolate was shown to eliminate the overgrowth of potential pathogenic bacteria in a mouse model (Stiefel et al., 2005). However, the present inventors found that this metallo-beta-lactamase preparation contained a mixture of beta-lactamase variants, which declines its value as a pharmaceutical protein, since variations of a drug substance reduce the robustness of the production process, increase batch to batch variations, and make clinical trials difficult, which of course has a negative impact on its registration as a medicament.

The present invention now provides means for reducing the amino terminal heterogeneity that was found to be associated with recombinant production of metallo-beta-lactamase. The invention further provides modified metallo-beta-lactamases that can be produced in substantially pure form and that can be used in the manufacture of pharmaceutical compositions.

SUMMARY OF THE INVENTION

The invention provides a modified metallo-beta-lactamase protein having the general formula:

NH₂—K-T-E-ΔBL-COOH  (I)

wherein
K is lysine
T is threonine
E is glutamic acid, and
ΔBL is a metallo-beta-lactamase protein that has been truncated at the amino terminal end so as to leave four beta-strands before the first alpha-helix of the predicted secondary structure of said protein.

The invention further provides an isolated nucleotide molecule comprising a nucleotide sequence encoding said modified metallo-beta-lactamase protein, as well as an expression vector containing the nucleotide molecule, and a host cell capable of expressing the metallo-beta-lactamase protein encoded by the nucleotide molecule.

The invention also provides a modified metallo-beta-lactamase protein having the general formula

NH₂-E-ΔBL-COOH  (II)

wherein
E and ΔBL are as defined above.

The invention still further provides a method of preparing a modified metallo-beta-lactamase protein, said method comprising culturing said host cell under conditions enabling the expression of a metallo-beta-lactamase having the general formula:

NH₂—K-T-E-ΔBL-COOH,  (I)

wherein
K is lysine
T is threonine
E is glutamic acid, and
ΔBL is a metallo-beta-lactamase protein that has been truncated at the amino terminal end so as to leave four beta-strands before the first alpha-helix of the predicted secondary structure of said protein,
and conducting post translational modification resulting in a modified metallo-beta-lactamase having the general formula:

NH₂-E-ΔBL-COOH,  (II)

wherein E and ΔBL are as defined above, and
optionally isolating and purifying the post translationally modified protein obtained.

As additional aspects the invention provides a pharmaceutical composition comprising the modified metallo-beta-lactamase protein of formula II, the modified metallo-beta-lactamase of formula II for use as a medicament, and the use of the modified metallo-beta-lactamase of formula II for the manufacture of a medicament for elimination of beta-lactam antibiotic induced adverse effects in the intestinal tract.

Finally the invention provides a method of treating beta-lactam anti-biotic induced adverse effects in the intestinal tract comprising administering an effective amount of the modified metallo-beta-lactamase of formula II, or the pharmaceutical composition containing it, to a person in need thereof. Specific embodiments of the invention are set forth in the dependent claims.

Other objects, details and advantages of the present invention will become apparent from the following drawings, detailed description and examples.

BRIEF DESCRIPTION OF THE DRAWINGS

FIG. 1 shows the complete nucleotide sequence (SEQ ID NO:4) and the deduced amino acid sequence (SEQ ID NO:1) of the *B. cereus* 98ME1552 beta-lactamase gene.

FIG. 2 shows the complete nucleotide sequence (SEQ ID NO:5) and the deduced amino acid sequence (SEQ ID NO:2) of the *B. cereus* 98ME1552 beta-lactamase gene derived from the pRSH315 expression construct. The cleavage site of the 31 amino acid residues long signal sequence of *Bacillus amyloliquefaciens* is predicted to occur between alanine at position −1 and glutamine at position +1. The $NH_2$-terminal extension of a $NH_2$-QAS-tripeptide that is derived from the Hind III cloning site is expressed in bold.

FIG. 3 shows the complete nucleotide sequence (SEQ ID NO:6) and the deduced amino acid sequence (SEQ ID NO:3) of the *B. cereus* 98ME1552 beta-lactamase gene derived from the pRSH318 expression construct. The cleavage of a 31 amino acid residues long signal sequence of *Bacillus amyloliquefaciens* is predicted to occur between alanine at position −1 and glutamine at position +1. The $NH_2$-terminal extension of the $NH_2$-QAS-tripeptide derived from the Hind III cloning site and the KT insertion are shown in bold.

DETAILED DESCRIPTION OF THE INVENTION

A metallo-beta-lactamase preparate was first produced in a *Bacillus subtilis* production system containing an expression construct of the complete metallo-beta-lactamase gene encoding the complete metallo-beta enzyme. Detailed mass spectrometry analysis revealed that the metallo enzyme preparate included various numbers of enzyme variants with heterogeneous amino terminal sequences. The variations at the amino terminus sequences were believed to be a result of post translational modification of host cell proteases. The observed alterations in the amino acid sequence of the metallo enzyme increase batch to batch variations of enzyme that has been produced in a *Bacillus subtilis* production system and thus in regulatory perspective reduce its use as a pharmaceutical protein. Therefore molecular biological means for reducing the observed variations in the amino terminal sequence of the metallo-beta-lactamase enzyme were studied.

The amino terminal region is expected to have no essential influence on the catalytic properties of the enzyme. In addition the amino terminal region was found to be exposed to post translational modifications of proteases in the *Bacillus subtilis* production system in which the recombinant protein is secreted outside the bacterial cell. In order to reduce this microheterogeneity in the amino terminal region, the nucleotide sequence encoding this predicted region was deleted by a PCR method. However, mere deletion by itself did not lead to a significant reduction of the amino terminal heterogeneity. Surprisingly, however, the deletion combined with insertion of a dipeptide, which was designed to assist post translational modification, led to a single metallo-beta-lactamase variant produced with an equally modified amino terminus.

This invention relates in general to a modified beta-lactamase useful as a pharmaceutical protein, and also to a recombinant beta-lactamase intermediate that is produced by truncation and insertion of a dipeptide at its amino terminal resulting in reduced numbers of beta-lactamase variants. These modifications facilitate the recombinant production of the enzyme in homologous form for use as a drug substance in beta-lactamase therapy for elimination of beta-lactams (cephalosporins, carbapenems, and penicillins in the presence or absence of known beta-lactamase inhibitors such as clavulanic acid, sulbactam and tazobactam) induced side effects. In particular the invention relates to targeted post translational modification of active metallo-beta-lactamase by truncation and insertion of a dipeptide at the amino terminal region to reduce amino terminal heterogeneity in a *Bacillus subtilis* production system.

"Metallo-beta-lactamases" as used herein refer to class B beta-lactamases i.e. beta-lactamases that require at least one bivalent metal ion ($Zn^{2+}$) for activity; and constitute group 3 in the in the Bush-Jacoby-Madeiros functional classification (Bush, 1998). Based on the structural similarities in the region that coordinates zinc binding, metallo-beta-lactamases can be divided into three subgroups, B1, B2, and B3 (Galleni et al., 2001). Preferably the metallo-beta-lactamase of the invention belongs to subgroup B1. This subgroup possesses the key zinc coordinating residues of three histidines and one cysteine. More details about the subgroups are set forth in the background part of this specification.

The metallo-beta-lactamases are members of a large, diverse, superfamily of proteins that share a similar four layered $\alpha\beta/\beta\alpha$ structure. The polypeptide chain is divided into two domains, which comprise strands and helices in the following order: $\beta_1\,\beta_2\,\beta_3\,\beta_4\,\beta_5\,\alpha_1\,\beta_6\,\alpha_2\,\beta_7\,\alpha_3$ and $\beta_8\,\beta_9\,\beta_{10}\,\beta_{11}\,\alpha_4\,\beta_{12}\,\alpha_5$, respectively (Carfi et al., 1995 and 1998a, and Galleni et al., 2001). The metallo-beta-lactamases of the invention are truncated at the amino terminal end prior to the second beta strand. Preferably they are truncated between the first and second beta strands, and in particular immediately in front of the amino acid E between the first and second beta strands according to the crystallographic structure above.

Garau et al., 2004 have set forth a standard numbering scheme for class B beta-lactamases (BBL) by analogy to Ambler beta-lactamase numbering (ABL) for serine beta-lactamases (Ambler, 1980). The BBL numbering scheme is derived from a structural alignment of known metallo-beta-lactamase X-ray structures in order to discover conserved regions among various metallo beta-lactamase groups having low degree of identity in primary amino acid sequence level. The study of Garau et al. revealed that the first conserved fragment forms the second beta sheet structure in *Bacillus cereus* BcII metallo beta-lactamase set forth by Carfi et al. 1995, and Carfi et al., 1998a. Consequently, the $\beta_1$-sheet of *B. cereus* metallo beta-lactamase appears to be non-essential for enzyme function, because it is not be present in all metallo beta-lactamase groups. However, the amino terminal region of all metallo beta-lactamases possess a secondary structure of four conserved beta sheets forming fragments before the first alpha helix forming fragment. Thus the truncation site for the metallo beta-lactamase may be defined as one leaving four beta strands before the first alpha helix of the predicted secondary structure regardless of the original presence of $\beta_1$ or not.

In the present context conventional one-letter amino acid codes and are used. Thus, A denotes alanine, R denotes arginine, N denotes asparagine, D denotes aspartic acid, C denotes cysteine, E denotes glutamic acid, Q denotes glutamine, G denotes glycine, H denotes histidine, I denotes isoleucine, L denotes leucine, K denotes lysine, M denotes methionine, F denotes phenylalanine, P denotes proline, S denotes serine, T denotes threonine, W denotes tryptophan, Y denotes tyrosine, and V denotes valine. The amino acid sequences are shown with the amino terminus to the left and carboxyl terminus to the right. $NH_2$— and —COOH may or may not be indicated.

According to one embodiment of the invention a host cell is transformed with an expression vector capable of expressing a beta-lactamase having the general formula I:

$$NH_2\text{—K-T-E-}\Delta\text{BL-COOH,} \qquad \text{(I)}$$

wherein K is lysine, T is threonine, E is glutamic acid, and ΔBL is a metallo-beta-lactamase protein that has been truncated at the amino terminal end prior to the second beta-strand of said protein, whereby a protein having the general formula II:

$$NH_2\text{-E-}\Delta\text{BL-COOH,} \qquad \text{(II)}$$

is formed as a result of post translational modification of the protein of formula I. The protein of the general formula I is conveniently produced by ligating a KT encoding DNA sequence to an E-ΔBL encoding DNA sequence, wherein E-ΔBL is a *Bacillus* and in particular a *B. cereus* metallo-beta-lactamase that has been truncated at the amino terminal end prior to the second beta strand immediately in front of a glutamic acid residue E. In particular the nucleotide construct comprises the sequential nucleotides 94-756 of SEQ ID NO:5.

The length of the amino terminal region without rigid structure varies between metallo-beta-lactamase groups and within each subclass. The metallo-beta-lactamases of *Bacillus* spp also possess variations in the amino terminal sequence prior to the second beta strand, but most enzymes have a conserved glutamic acid (E) at position +12 (see Table 1). Consequently, the deletion coupled with the KT insertion adjacent to E can be applied to known *Bacillus* metallo-beta-lactamases, in which case the first eleven amino terminal amino acids are deleted from the N-terminal end of the naturally occurring mature beta-lactamase protein. According to one specific embodiment of the invention the beta-lactamase is truncated between the amino acids KN and E, and especially between VIKN and E, or VMKN and E.

TABLE 1

Comparison of the amino terminal sequences between *Bacillus* sp metallo-beta-lactamases and P2A.

| Protein | *Bacillus* strain | Amino terminal region |
|---|---|---|
| P2A | *B. cereus* 98ME1552 | EQKLEQIVIKNETGTISISQLNK (SEQ ID NO: 8) |
| Q2AJV1 | *B. weihenstephanensis* KBAB4 | EQKLEQKVIKNETGTISISQLNK (SEQ ID NO: 9) |
| P10425 | *Bacillus* sp. (strain 170) | SQKVEQIVIKNETGTISISQLNK (SEQ ID NO: 10) |
| Q734F3 | *B. cereus* ATCC 10987 | EQKLEQKVIKNEAGTISISQLNK (SEQ ID NO: 11) |
| P04190 | *B. cereus* 569/H | SQKVEKTVIKNETGTISISQLNK (SEQ ID NO: 12) |
| Q81AW2 | *B. cereus* ATCC 14579/DSM 31 | SQKVEKTVIKNETGTISISQLNK (SEQ ID NO: 13) |
| Q93T40 | *B. anthracis* Sterne | ERKVEHKVIKNETGTISISQLNK (SEQ ID NO: 14) |
| Q6SPY5 | Penicillin resistant *B. anthracis* | ERKVEHKVIKNETGTISISQLNK (SEQ ID NO: 15) |
| Q4MXZ5 | *B. cereus* G9241 | SQKVEQKVMKNEAGTISISQLNK (SEQ ID NO: 16) |
| P14488 | *B. cereus* 5/B/6 | ERTVEHKVIKNETGTISISQLNK (SEQ ID NO: 17) |
| Q6HFY5 | *B. thuringiensis* 97-27 | ERTVEHKVIKNETGTISISQLNK (SEQ ID NO: 18) |

*The amino acid substitutions are bolded and the conserved glutamic acid (E) is shaded. The first beta strand for metallo-beta-lactamases is once underlined, and the second beta strand is twice underlined.

According to a specific embodiment of the invention E-ΔBL has at least 70, 80, 90, 95, 98 or 99% identity to the amino acid sequence of sequential amino acid residues 6-221 of SEQ ID NO: 3. Sequence identity may be determined using BLAST (Basic Local Alignment Search Tools) as described in Altschul et al., 1997. In particular E-ΔBL is a truncated form of a metallo-beta-lactamase having the sequence as set forth as SEQ ID NO: 1, or a beta-lactamase active variant or fragment thereof. It may e.g. be a truncated form of *B. cereus* metallo-beta-lactamase BcII. Preferably E-ΔBL has an amino terminal end that corresponds to amino acid residues 12-15, 12-19, or 12-23 of SEQ ID NO: 1, with the addition that the amino acid at position +13 may be either T (threonine) or A (alanine).

By an amino acid sequence that is a "variant" of a specific amino acid sequence is meant an amino acid sequence that is not identical to the specific amino acid sequence, but contains at least some amino acid changes i.e. deletions, substitutions, inversions, insertions etc. that do not essentially affect the biological activity of the protein as compared to that of the specific amino acid sequence. Biological activity in this context refers to beta-lactamase activity. A variant may be a polypeptide that occurs naturally e.g. as an allelic variant within the same strain, species or genus, or it may have been generated by mutagenesis.

A "fragment" is understood to be part of a specific amino acid sequence that is long enough to have the desired biological activity i.e. beta-lactamase activity. In other words the fragment may be e.g. a subsequence of the specifically disclosed beta-lactamases.

The nucleotide construct encoding NH$_2$—K-T-E-ΔBL-COOH may be inserted in an expression vector, and transformed into a host cell. The host cell is then cultivated under conditions enabling expression and post translational modification of the protein into NH$_2$-E-ΔBL-COOH, which thus may be obtained in substantially pure form, which means that at least 90%, and preferably at least 95%, in particular at least 99% of the metallo-beta-lactamase is present in a single form as NH$_2$-E-ΔBL-COOH. The post translational modification of the expressed protein, i.e. the cleavage of the dipeptide KT is catalyzed by proteases of the host. The host may be eukaryotic or prokaryotic, such as a bacterial, yeast or fungus cell. The bacterial host may be e.g. *Escherichia coli*. Preferably the host belongs to *Bacillus* spp, and in particular it is *B. licheniformis* or *B. subtilis*. According to one preferred embodiment the NH$_2$—K-T-E-ΔBL-COOH is expressed as a protein comprising a signal peptide, whereby the protein is secreted into the culture medium, and the signal peptide is first cleaved, and then the dipeptide. Minor other changes such as deamidation, oxidation, disulfide bond breakage or formation, isomerization, succinimidation, non-disulfide crosslinking, Maillard reaction, deglycosylation may occur in the protein during the production process or storage, and are acceptable as long as the beta-lactamase activity is not significantly affected.

The modified beta-lactamase NH$_2$-E-ΔBL-COOH may originate from any bacterium capable of producing a metallo-beta-lactamase. Such bacteria are e.g. bacteria of the *Enterobacteriae* genus (*Serratia marcescens*, *Klebsiella pneumoniae*, *Citrobacter freudii*, *Shigella flexneri*), *Pseudomonas aeruginosa*, *Stenobacterium maltophila*, *Acinetobacter* genus, *Bacteroides fragilis*, *Bacillus cereus*, *Flavobacteruim odoratum*, and *Bacteroides fragilis*. Other possible sources are *Aeromonas*, *Legionella* and *Stenotrophomonas* species.

The enzyme is truncated at the amino terminal end of the mature enzyme protein prior to the second beta strand at a position resulting in E as the N-terminal amino acid. If there is no appropriate residue E in the bacterial beta-lactamase, only the ΔBL part may be obtained from the bacterium, whereas a tripeptide KTE is coupled in front of ΔBL to from the protein NH$_2$—K-T-E-ΔBL-COOH.

Preferably the modified beta-lactamase is derived from Bacillus, and especially from B. cereus. In particular it is a B. cereus beta-lactamase from which the first eleven N-terminal amino acids of the non-modified mature beta-lactamase protein have been deleted.

The modified beta-lactamase of the invention may be mixed with any pharmaceutically acceptable excipients or carriers to form a pharmaceutical composition. An amount of the modified beta-lactamase effective of eliminating the adverse effect of beta-lactam antibiotics in the intestine is then administered orally to a person being treated with one or more beta-lactam antibiotics. The beta-lactamase preparation may be administered before, simultaneously with, or after the antibiotic treatment. It is insensitive to serine beta-lactamase inhibitors, and may therefore be used to eliminate the antibiotic both in the presence and absence of such inhibitors.

The invention is illustrated by the following non-limiting examples. It should be understood, however, that the embodiments given in the description above and in the examples are for illustrative purposes only, and that various changes and modifications are possible within the scope of the invention.

EXAMPLE 1

Materials and Methods

Bacterial Strains and Growth Conditions

The bacterial strains and their relevant genotypes and phenotypes are presented in Table 2.

TABLE 2

Bacterial strains and their relevant genotypes and phenotypes

| Strain | Relevant genotype | Relevant phenotype |
|---|---|---|
| *Bacillus subtilis* RS303 | trpC2, sigG::cat (Δ sigG) | Tryptophan auxotroph, asporogenic |
| *Bacillus subtilis* IH 6140 | sacA321 | Reduced exoprotease level |
| *Bacillus subtilis* RS314 | trpC2, sigG::cat, (Δ sigG) pRSH314 expression construct encoding the truncated metallo-beta-lactamase | Tryptophan auxotroph, asporogenic, secretes metallo-beta-lactamase |
| *Bacillus subtilis* RS315 | trpC2, sigG::cat, (Δ sigG) pRSH315 expression construct encoding the complete metallo-beta-lactamase gene | Tryptophan auxotroph, asporogenic, secretes metallo-beta-lactamase |
| *Bacillus subtilis* RS317 | trpC2, sigG::cat, (Δ sigG) pRSH317 expression construct encoding truncated metallo-beta-lactamase | Tryptophan auxotroph, asporogenic, secretes metallo-beta-lactamase |
| *Bacillus subtilis* RS318 | trpC2, sigG::cat, (Δ sigG) pRSH318 expression construct encoding truncated metallo-beta-lactamase | Tryptophan auxotroph, asporogenic, secretes metallo-beta-lactamase |
| *Bacillus cereus* 98ME1552 | | Multiresistant to various beta-lactams |

Bacteria were generally cultivated in complex Luria medium (5 grams of yeast extract, 10 grams of tryptone and 10 grams of sodium chloride per litre) supplemented with appropriate antibiotics as selection agents in shaking flask mode at +37° C. A synthetic culture medium supplemented with appropriate antibiotic was used in fermentations. A modified synthetic medium was used to generate competent *Bacillus subtilis* cells. Detailed composition of these media is described in WO03/040352.

DNA Techniques

Conventional DNA techniques including e.g. restrictions, agarose gel electrophoresis and ligations, were performed according to Sambrook and Russell (2001). The chromosomal DNA was isolated by the Marmur method (Marmur, 1961). The plasmid DNA was isolated by Qiagen plasmid Midi Kit according to manufacturer's instructions (Qiagen Plasmid Purification Handbook, 1999) but lysozyme treatment (1 mg/ml) was added to the protocol in order to degrade the peptidoglycan layer. Lysozyme was supplemented to buffer P1 and cells were incubated at 37° C. for 30 minutes.

PCR was generally performed according to protocols described in WO03/040352.

Characterization of Amino Terminal Region of Various Forms of Metallo-Beta-Lactamase For determinations of the N-terminal amino acid sequence and mass spectrometry, purified metallo-beta-lactamase samples were subjected to reverse phase chromatography and the enzymes were fractioned in a linear gradient of 0.1% of TFA and 0.075% TFA-acetonitrile from 0% to 100% for 60 minutes.

$NH_2$-terminal sequences of metallo-beta-lactamase forms were determined by automated Edman degradation with an Applied Biosystems model 494A Protein Sequenator.

Mass analyses of metallo-beta-lactamase forms were performed by a hybrid quadrupole-time-of-flight (Q-TOF) instrument. Metallo-beta-lactamase variants have been assumed to provide comparable ionization potentials which have been utilized in the assessments of their relative proportions in the samples.

The nucleotide sequences of the beta-lactamase genes were determined by the dideoxy-chain termination method with an automatic DNA sequencer.

EXAMPLE 2

The Complete Nucleotide Sequence of *Bacillus cereus* 98ME1552 Metallo-Beta-Lactamase Gene The determination of the complete gene coding metallo-beta-lactamase was sequentially performed by using PCR and Vectorette techniques. Part of the structural gene was amplified by PCR, with isolated chromosomal DNA of a clinical isolate *B. cereus* 98ME1552 as a template and with primers designed to hybridize to the SQKVEKTVI (SEQ ID NO:19) coding region (forward primer) and HTLDLL (SEQ ID NO:20) coding region (reverse primer) of the *Bacillus cereus* 569/H metallo-beta-lactamase gene. Both primers also carry Hind III restriction sites. The amplified DNA fragment (about 700 bp) was digested with Hind III and ligated to the Hind III site of a secretion vector pKTH141. Competent *Bacillus subtilis* IH6140 cells were transformed with the ligation mixture. A clone harboring a plasmid expressing metallo-beta-lactamase was verified by DNA sequencing. The plasmid was named pRSH314.

Competent *B. subtilis* RS303 cells prepared as described in WO03/04052 were transformed with pRSH314 resulting in strain *B. subtilis* RS314.

The complete DNA sequence of metallo-beta-lactamase gene was determined from PCR fragments obtained by employing Vectorette technique as follows: The chromosomal DNA of *Bacillus cereus* 98ME1552 was digested with Hind III restriction enzyme and ligated to Hind III treated VectoretteII. The obtained Vectorette-library was screened in a PCR reaction by employing the MEBLSQ-F (SEQ ID NO:21) (5'-AGGAAATGTTGCGGATGC) (SEQ ID NO:22) or MEBLSQ-R (SEQ ID NO:21) (5'-CCTTCGTTAATTTGTTATCCC) (SEQ ID NO:23) initiating primers designed from the DNA sequence obtained from the 700 bp of pRSH314.

PCR screening of the Vectorette library with the MEBLSQ-F primer generated a fragment of about 1000 bp (MEBL1 fragment) and with the MEBLSQ-R primer a fragment of about 1100 bp (MEBL2 fragment). Both MEBL1 and MEBL2 fragments were purified from agarose gel after electrophoresis. The nucleotide sequences of both fragments were determined by DNA sequencing resulting in the complete nucleotide of *B. cereus* 98ME1552 metallo-beta-lactamase gene. The complete nucleotide and deduced amino acid sequence of the *B. cereus* 98ME1552 metallo-beta-lactamase gene is presented in FIG. 1. The amino acid sequence is also set forth as SEQ ID NO: 1. The open reading frame encodes a 257 amino acid polypeptide, whose amino terminal sequence (30 amino acid residues) exhibits features typical of those of a bacterial signal peptide that targets protein secretion across the cytoplasmic membrane via a general secretory pathway. The predicted signal peptidase cleavage site is after alanine at position of −30 (see FIG. 1.). The calculated molecular mass and the pI value of the mature protein of 227 amino acid residues is 24 877.3 Da and 6.0, respectively. The 98ME1552 metallo-beta-lactamase sequence was used as a search template in a BLAST search in order to identify the protein. The BLAST search was performed using the SIB BLAST Network Service of Swiss Institute of Bioinformatics (Worldwide Website: expasy.org/tools/blast/). The search was done against a UniProtKB Knowledge based database using the NCBI BLASTP 2.2.13 program (Altschul et al., 1997) with BLOSUM62 algorithm and gap penalties 11 for existence and 1 for extension. The BLAST search performed with the 98ME1552 metallo-beta-lactamase gave the highest similarity scored with other class B beta-lactamases of subgroup B1. As expected, the 98ME1552 beta-lactamase exhibited a high degree of identity (over 90%) to other *B. cereus* beta-lactamases. According to structural alignment of various *B. cereus* metallo-beta-lactamase, the amino acid substitutions in *B. cereus* 98ME1552 lactamase are predicted to locate in regions not essential for the function of the enzyme.

EXAMPLE 3

Cloning and Expression of the *B. cereus* 98ME1552 Metallo-Beta-Lactamase Gene in *Bacillus subtilis*

Based on the obtained DNA sequences from the Vectorette library new primers,

```
BLC1-F
(5'-CGCGAAGCTTCCGAACAAAAGCTAGAGCAAATAGTAATC),
and

BLC1-R
(5'-
GCCGAAGCTTTTATTTTAATAAATCCAATGTATGTAAAAGTAATCCC)
``` were designed to generate a DNA insert encoding the complete metallo-beta-lactamase in PCR. The primers also carried Hind III-sites at their ends and purified chromosomal DNA of *B. cereus* 98ME1552 was used as a template. The amplified PCR fragment of about 0.7 kb was digested with Hind III and ligated to the Hind III site of a pKTH141 secretion vector. Competent *Bacillus subtilis* RS303 cells were transformed by the ligation mixture. One positive clone was designated RS315 and the harboring expression construct was named pRSH315.

The pRSH315 expression construct was isolated and the insert region was sequenced. The nucleotide and deduced amino acid sequences of the cloned metallo-beta-lactamase gene were identical to those determined from the Vectorette library. The determined DNA sequence revealed in frame fusion between the nucleotide sequence encoding a 31 amino acid long signal sequence of *Bacillus amyloliquefaciens* alpha amylase, the Hind III cloning site and the complete *B. cereus* 98ME1552 metallo-beta-lactamase gene (see FIG. 2). Signal peptidase is predicted to cut the peptide bond between alanine (A) at position of −1 and glutamine (Q) at position of +1. The mature metallo-beta-lactamase possesses an $NH_2$-terminal extension of a $NH_2$-QAS-tripeptide that is derived from the Hind III cloning site in the expression construct. Hence, based on the deduced amino acid sequence the mature modified metallo-beta-lactamase is comprised of 230 amino acid residues.

EXAMPLE 4

Determination of the Amino Terminal Amino Acid Sequence of Metallo-Beta-Lactamase Variants Obtained from a *Bacillus subtilis* Production System For further characterization, the recombinant metallo-beta-lactamase was produced in cultivations performed in either shaking flask or fermentation by using a synthetic growth medium. The metallo-beta-lactamase was effectively secreted into the culture supernatant. The enzyme was purified from concentrated culture supernatant by ion exchange chromatography. Enzyme activity was observed in two separate fractions. Purified enzyme fractions were subjected to $NH_2$-terminal sequencing and mass spectrometry analysis. Analyses revealed that both fractions comprised enzyme forms with heterogeneous amino terminus. The various enzyme forms and their relative proportions are presented in Table 3. Related to the deduced amino acid sequence, all enzyme forms have deletions of various lengths in their NH$_2$-terminal regions. In general, the NH$_2$-QASEQKLE (SEQ ID NO:39) octapeptide seems to be deleted in all enzyme forms. Furthermore the smallest enzyme form in fraction 2 lacks an additional IVIKN (SEQ ID NO:40)-pentapeptide. The observed microheterogeneity in the NH$_2$-terminal region can be explained as post translational modifications caused by the action of various host cell proteases.

of the expression construct isolated from a positive clone. The transformant strain was named *Bacillus subtilis* RS317 and the expression construct was called pRSH317.

Truncated metallo-beta-lactamase was produced in a *Bacillus subtilis* production host and the enzyme was purified from the culture supernatant by employing ion change chromatography from which the active enzyme was eluted as a single fraction. The enzyme fraction was subjected to NH$_2$-terminal amino acid sequencing and molecular mass analysis.

TABLE 3

Deduced and determined amino terminal sequences and determined molecular mass of truncated metallo-beta-lactamase forms

| Enzyme fraction n:o | Deduced NH$_2$-terminal amino acid sequence | Determined NH$_2$-terminal sequence | Relative proportion of enzyme forms in fractions (%) | Determined Mass (kDa) |
|---|---|---|---|---|
| 1 | NH$_2$-QASEQKLEQIVIKNETGTI | NH$_2$-IVIKNETGTI | 100 | 24.122 |
| 2 | | NH$_2$-NETGTI | 60 | 23.668 |
| 2 | | NH$_2$-ETGTI | 40 | 23.554 |

EXAMPLE 5

Construction of *Bacillus cereus* 98ME1552 Deleted Metallo-Beta-Lactamase Form and its Amino Terminal Variants in a *Bacillus subtilis* Production System In order to try to reduce $NH_2$-terminal heterogeneity the DNA sequence encoding the variable region $NH_2$-EQKLEQIVIKN (SEQ ID NO:31) of the metallo-beta-lactamase gene was deleted by PCR. The complete gene of *B. cereus* 98ME1552 metallo-beta-lactamase was used as a template in *PCR with a forward primer hybridizing to a ETGTISISQ (SEQ ID NO:32) coding sequence and a reverse primer hybridizing to a GLLLHTLDLLK (SEC) ID NO:33) coding sequence followed by a translation stop codon TAA. Both primers carried Hind III sites.*

The obtained PCR fragment of about 0.7 kb was cloned into the Hind III site of the pKTH141 secretion vector and the competent *B. subtilis* RS303 strain was transformed by the ligation mixture. The $NH_2$-terminal deletion was verified by DNA sequencing of the inserted metallo-beta-lactamase gene The observed results (in Table 4) showed that the truncated metallo-beta-lactamase also appeared as a protein with a heterogeneous amino terminus. The major enzyme variant possesses an amino-terminal sequence identical to that of the deduced amino acid sequence including the Hind III site coding the initiation QAS-tripeptide. A minor variant was found to have a deletion of a QA-dipeptide. Due to amino terminal blockage, no amino acid sequence was received from one variant. Amino terminal blockage is likely to be the result of cyclization of the glutamine residue to form a pyroglutamyl residue during the production process. To conclude, the amino terminal deletion did not fundamentally reduce amino terminal microheterogeneity.

TABLE 4

Determined amino terminal sequences and molecular masses of truncated metallo-beta-lactamase forms.

| Enzyme fraction n:o | Deduced $NH_2$-terminal amino acid sequence | Determined $NH_2$-terminal sequence | Relative proportion of enzyme forms in fractions (%) | Mass analysis (kDa) |
|---|---|---|---|---|
| 1. | $NH_2$-QASETGTISI | a. cyclic form of glutamine → no amino acid sequence | | a. 23.823 |
| | | b. $NH_2$-QASETGTISI | b. 90 | b. 23.840 |
| | | c. $NH_2$-SETGTISI | c. 10 | c. 23.641 |

EXAMPLE 6

Construction of *Bacillus cereus* 98ME1552 Truncated Metallo-Beta-Lactamase Possessing a KT Coding Sequence Insert In order to avoid post translational modification a molecular truncation of metallo-beta-lactamase was designed to comprise the deletion of the DNA sequence coding the $NH_2$-EQKLEQIVIKN (SEQ ID NO:36) region together with insertion of a KT dipeptide coding sequence located directly downstream of the 3'-Hind III cloning site.

A modified metallo-beta-lactamase gene was created as in Example 5, except for the forward primer, which contained a KT coding DNA sequence. The PCR fragment was cut with Hind III and ligated to the Hind III site of the pKTH141 secretion vector and competent *B. subtilis* RS303 cells were transformed by the ligation mixture. The correct nucleotide sequence of the modified metallo-beta-lactamase gene in the expression construct was confirmed by DNA sequencing. One positive clone was named *Bacillus subtilis* RS318 and the expression construct was called pRSH318. The nucleotide and the deduced amino acid sequence of the *B. cereus* 98ME1552 beta-lactamase derived from pRSH318 is presented in FIG. 3, and set forth as SEQ ID NOs: 5 and 6 (nucleotide sequences) and 2 and 3 (amino acid sequences), respectively.

The truncated metallo-beta-lactamase was produced, purified, and analyzed as earlier described. The active truncated metallo enzyme was eluted from the column as a single peak. The single fraction contained metallo-beta-lactamase that possessed a homologous amino terminal glutamic acid residue ($NH_2$-E; see Table 5). Accordingly, the KT-dipeptide insertion conducts post translational modification resulting in a uniform amino terminal amino acid sequence. The truncated metallo-beta-lactamase was named the P2A protein.

TABLE 5

Deduced and determined amino terminal sequences and the determined molecular mass of truncated metallo-beta-lactamase form

| Enzyme fraction n:o | Deduced $NH_2$-terminal amino acid sequence | Determined $NH_2$-terminal sequence | Relative proportion of enzyme forms in fractions (%) | Mass analysis (kDa) |
|---|---|---|---|---|
| 1. | $NH_2$-QASKTETGTISI | a. $NH_2$-ETGTISI | a. 100 | a. 23554 |

EXAMPLE 7

Kinetic Enzyme Parameters of the P2A Metallo-Beta-Lactamase

Diversity of the catalytic properties of the P2A enzyme was studied with various types of beta-lactams including the penicillin family with and without serine beta-lactamase inhibitors, second and third generation cephalosporins, and carbapenems (meropenem). The enzyme kinetic parameters $k_{cat}$ and $K_m$ were determined from initial rates by Hanes plot. The reactions were performed in 10 mM phosphate buffer, pH 7.0 at 30° C. The reaction cuvette (one mL) contained about 5 pmol of enzyme in all reactions except 1.7 pmol of enzyme in the meropenem assay. The hydrolysis of various beta-lactam substrates was spectrophometrically recorded at a wavelength specific for each substrate.

Values for different kinetic parameters ($k_{cat}$, $K_m$ and $k_{cat}/K_m$) that represent mean values obtained from three independent measurements are reported in Table 6.

TABLE 6

Kinetic parameter values for the P2A metallo-beta-lactamase

| | The P2A protein | | |
|---|---|---|---|
| Antibiotic | $K_m$ (microM) | $k_{cat}$ (1/s) | $k_{cat}/K_m$ ($M^{-1} \times s^{-1}$) |
| Ampicillin | 942 | 1114 | $1.18 \times 10^{-6}$ |
| Ampicillin-sulbactam (Unasyn) | 1104 | 1251 | $1.15 \times 10^{-6}$ |

TABLE 6-continued

Kinetic parameter values for the P2A metallo-beta-lactamase

| | The P2A protein | | |
|---|---|---|---|
| Antibiotic | $K_m$ (microM) | $k_{cat}$ (1/s) | $k_{cat}/K_m$ ($M^{-1} \times s^{-1}$) |
| Amoxycillin | 716 | 980 | $1.37 \times 10^{-6}$ |
| Amoxycillin-clavulanic acid (Augmentin) | 717 | 990 | $1.38 \times 10^{-6}$ |
| Piperacillin | 372 | 1049 | $2.82 \times 10^{-6}$ |
| Piperacillin-tazobactam (Tazocin) | 412 | 1098 | $2.67 \times 10^{-6}$ |
| Cefuroxime | 27 | 221 | $7.99 \times 10^{-6}$ |
| Cefotaxime | 66 | 479 | $7.28 \times 10^{-6}$ |
| Ceftriaxone | 68 | 95 | $1.40 \times 10^{-6}$ |
| Meropenem | 410 | 480 | $1.17 \times 10^{-6}$ |

EXAMPLE 8

Stability of the P2A Protein in Human Ileal Chyme

Resistance to intestinal proteases is one of the most important factors affecting the applicability of the P2A protein as a drug substance in targeted beta-lactamase therapy in the small intestine. The susceptibility of metallo-beta-lactamase to the action of small intestinal proteases was tested by adding various amounts of active enzyme in tubes consisting human ileal chyme. The hydrolysis of metallo-beta-lactamase was monitored by measuring beta-lactamase activity of ileal samples at various time points. Meropenem was employed as substrate in the activity assays.

The obtained results from four independent experiments and the mean values are expressed in Table 7. The P2A enzyme appears to be a stable protein, which was cleared in human ileal chyme with a half-life of 55 minutes (mean value). High variations of half-lives were observed between various experiments. However, the half-life of P2A in human small intestinal chyme has been evaluated to be adequate for successful application of P2A enzyme therapy for elimination of residual beta-lactam induced adverse reaction in the intestinal tracts.

TABLE 7

Half-life (in vitro) of the P2A metallo-beta-lactamase in human ileal chyme.

| Experiment n: o | Half-life (minutes) | Mean value (±SD) |
|---|---|---|
| 1 | 60 | 55 ± 25 |
| 2 | 80 | 55 ± 25 |
| 3 | 20 | 55 ± 25 |
| 4 | 60 | 55 ± 25 |

REFERENCES

Altschul S. F., Madden T. L., Schäffer A. A., Zhang J., Zhang Z., Miller W., Lipman D. J. 1997. Gapped BLAST and PSI-BLAST: a new generation of protein database search programs. Nucleic Acids Res. 25: 3389-3402

Ambler, R. P. 1980. The structure of beta-lactamases. Philos. Trans. R. Soc. London B 289:321-331.

Bush, K. 1998. Metallo-β-lactamases: a class apart. Clin. Infect. Dis. 32: 271-276.

Carfi A, Duee E, Galleni M, Frere J M, and Dideberg O. 1998a. 1.85 A resolution structure of the zinc (II) beta-lactamase from *Bacillus cereus*. Acta Crystallogr D Biol Crystallogr. 54:313-323.

Carfi A, Duee E, Paul-Soto R, Galleni M, Frere J M, and Dideberg O. 1998b. X-ray structure of the ZnII beta-lactamase from *Bacteroides fragilis* in an orthorhombic crystal form.

Acta Crystallogr D Biol Crystallogr. 54:45-57.

Carfi, A., Pares, S., Duee, E., Galleni, M., Duez, C., Frere, J. M., and Dideberg O. 1995. The 3-D structure of a zinc metallo-beta-lactamase from *Bacillus cereus* reveals a new type of protein fold.

EMBO J. 14:4914-4921.

Concha, N. O., Janson, C. A., Rowling, P., Pearson, S., Cheever, C. A, Clarke, B. P., Lewis, C., Galleni, M., Frere, J. M., Payne, D. J., Bateson, J. H., and Abdel-Meguld, S. S. 2000. Crystal structure of the IMP-1 metallo beta-lactamase from *Pseudomonas aeruginosa* and its complex with a mercaptocarboxylate inhibitor: binding determinants of a potent, broad-spectrum inhibitor. Biochemistry. 39:4288-4298.

Galleni, M., Lamotte-Brasseur, J., Rossolini, G. M., Spencer, J., Dideberg, O., and Frere, J. M. 2001. Metallo-beta-lactamases Standard numbering scheme for class B beta-lactamases.

Antimicrob. Agents Chemother. 45:660-663

Garau, G., Garcia-Saez, I., Bebrone, C., Anne, C., Mercuri, P., Galleni, M., Frere, J. M., and Dideberg, O. 2004. Update of the standard numbering scheme for class B beta-lactamases. Antimicrob. Agents Chemother. 48:2347-2349.

Garau, G., Bebrone, C., Anne, C., Galleni, M., Frere, J. M., Dideberg, O. 2005. A metallo-beta-lactamase enzyme in action: crystal structures of the monozinc carbapenemase CphA and its complex with biapenem. J Mol Biol. 345: 785-795.

Harmoinen, J., Mentula, S., Heikkilä, M., van der Rest M., Rajala-Schultz, P. J., Donskey, C. J., Frias, R., Koski, P., Wickstrand, N., Jousimies-Somer, H., Westermarck, E., Lindevall, K. 2004. Oral Targeted Recombinant Beta-Lactamase Prevents Ampicillin-Induced Selective Pressure on the Gut Microbiota: A Novel Approach to Reduce Antimicrobial Resistance Antimicrob. Agents and Chemotherapy. 48: 75-79.

Marmur, J. 1961. A procedure for the isolation of deoxyribonucleic acid from micro-organisms. J. Mol. Biol. 3: 208-218.

Mentula, S., Harmoinen, J., Koski, P., Westermarck, E., Huovinen, P., and Könönen, E. 2004. Inhibition of ampicillin-induced emergence of resistance in intestinal coliforms by targeted recombinant beta-lactamase. Int. J. Antimicrob. Agents. 24:555-561.

Sambrook, J., and Russell, D. W. 2001. Molecular cloning, a Laboratory Manual. Cold Spring Harbour Laboratory Press Cold Spring Harbour, N.Y.

Stiefel, U., Pultz, N. J., Harmoinen, J., Koski, P., Lindevall, K., Helfand, M. S., Donskey, C. J. 2003. Oral β-lactamase administration preserves colonization resistance of piperacillin-treated mice. J Infect Dis. 10: 1605-1609.

Stiefel, U., Harmoinen, J., Koski, P., Kaariainen, S., Wickstrand, N., Lindevall, K., Pultz, N. J., Bonomo, R. A., Helfand, M. S., and Donskey, C. J. 2005. Orally administered recombinant metallo-beta-lactamase preserves colonization resistance of piperacillin-tazobactam-treated mice. Antimicrob. Agents Chemother. 49: 5190-5191.

Walsh, T. R., Toleman, M. A., Poirel, L., and Nordmann, P. 2005. Metallo-beta-lactamases: the quiet before the storm? Clin Microbiol Rev. 18:306-325

---

The invention claimed is:

1. A truncated metallo-beta-lactamase protein having the general formula $$NH_2\text{-}E\text{-}\Delta BL\text{-}COOH$$

wherein

E is glutamic acid, and

ΔBL is a metallo-beta-lactamase protein that has been truncated at the amino terminal end so as to leave four beta-strands before the first alpha-helix of the predicted secondary structure of said protein, wherein E-ΔBL has an amino terminal end that corresponds to amino acid residues 12-15 of SEQ ID NO:1, and the amino acid at position +13 is either threonine or alanine.

2. The metallo-beta-lactamase protein of claim 1, which belongs to subgroup B1 of metallo-beta-lactamases.

3. The metallo-beta-lactamase protein of claim 2, wherein the truncated beta-lactamase is obtained from *Bacillus* spp, and especially from *B. cereus*.

4. The metallo-beta-lactamase of claim 3, wherein E-ΔBL is obtained by deleting the first eleven amino terminal amino acids of a mature metallo-beta-lactamase.

5. The metallo-beta-lactamase of claim 2, wherein E-ΔBL is obtained by truncation of a metallo-beta-lactamase between the amino acids KN and E.

6. A pharmaceutical composition comprising the truncated modified metallo-beta-lactamase protein of claim 1.

7. The truncated metallo-beta-lactamase of claim 1, wherein E-ΔBL has an amino terminal end that corresponds to amino acid residues 12-19 of SEQ ID NO:1, and the amino acid at position +13 is either threonine or alanine.

8. The truncated metallo-beta-lactamase of claim 1, wherein E-ΔBL has an amino terminal end that corresponds to amino acid residues 12-23 of SEQ ID NO:1, and the amino acid at position +13 is either threonine or alanine.

9. The metallo-beta-lactamase protein of claim 2, wherein the sequence E-ΔBL has at least 90% identity to the amino acid sequence of sequential amino acid residues 6-221 of SEQ ID NO:3.

10. The metallo-beta-lactamase protein of claim 2, wherein the sequence E-ΔBL has at least 95% identity to the amino acid sequence of sequential amino acid residues 6-221 of SEQ ID NO:3.

11. The metallo-beta-lactamase protein of claim 2, wherein the sequence E-ΔBL has at least 98% identity to the amino acid sequence of sequential amino acid residues 6-221 of SEQ ID NO:3.

12. The pharmaceutical composition of claim 6, wherein at least 90% of the metallo-beta-lactamase is present in a single form as the metallo-beta-lactamase of claim 8.

* * * * *

SEQUENCE LISTING

```
<160> NUMBER OF SEQ ID NOS: 41

<210> SEQ ID NO 1
<211> LENGTH: 257
<212> TYPE: PRT
<213> ORGANISM: Bacillus cereus
<220> FEATURE:
<221> NAME/KEY: mat_peptide
<222> LOCATION: (31)..(257)

<400> SEQUENCE: 1

Met Lys Lys Asn Thr Leu Leu Lys Leu Gly Val Cys Val Ser Leu Leu
-30                 -25                 -20                 -15

Gly Ile Thr Gln Phe Val Ser Thr Ile Ser Ser Val Lys Ala Glu Gln
                -10                  -5                  -1   1

Lys Leu Glu Gln Ile Val Ile Lys Asn Glu Thr Gly Thr Ile Ser Ile
             5                  10                  15

Ser Gln Leu Asn Lys Asn Val Trp Val His Thr Glu Leu Gly Tyr Phe
             20                  25                  30

Asn Gly Glu Ala Val Pro Ser Asn Gly Leu Val Leu Asn Thr Ser Lys
35                  40                  45                  50
```

```
Gly Leu Val Leu Val Asp Ser Ser Trp Asp Asn Lys Leu Thr Lys Glu
                    55                  60                  65

Leu Ile Glu Met Val Glu Lys Lys Phe Gln Lys Arg Val Thr Asp Val
            70                  75                  80

Ile Ile Thr His Ala His Ala Asp Arg Ile Gly Gly Ile Thr Ala Leu
        85                  90                  95

Lys Glu Arg Gly Ile Lys Ala His Ser Thr Ala Leu Thr Ala Glu Leu
    100                 105                 110

Ala Lys Asn Ser Gly Tyr Glu Glu Pro Leu Gly Asp Leu Gln Thr Ile
115                 120                 125                 130

Thr Ser Leu Lys Phe Gly Asn Thr Lys Val Glu Thr Phe Tyr Pro Gly
                135                 140                 145

Lys Gly His Thr Glu Asp Asn Ile Val Val Trp Leu Pro Gln Tyr Gln
            150                 155                 160

Ile Leu Ala Gly Gly Cys Leu Val Lys Ser Ala Glu Ala Lys Asp Leu
        165                 170                 175

Gly Asn Val Ala Asp Ala Tyr Val Asn Glu Trp Ser Thr Ser Ile Glu
    180                 185                 190

Asn Val Leu Lys Arg Tyr Gly Asn Ile Asn Ser Val Val Pro Gly His
195                 200                 205                 210

Gly Glu Val Gly Asp Lys Gly Leu Leu Leu His Thr Leu Asp Leu Leu
                215                 220                 225

Lys

<210> SEQ ID NO 2
<211> LENGTH: 261
<212> TYPE: PRT
<213> ORGANISM: Bacillus cereus
<220> FEATURE:
<221> NAME/KEY: sig_peptide
<222> LOCATION: (1)..(93)

<400> S

```
            180                 185                 190

Pro Gln Tyr Gln Ile Leu Ala Gly Gly Cys Leu Val Lys Ser Ala Glu
        195                 200                 205

Ala Lys Asp Leu Gly Asn Val Ala Asp Ala Tyr Val Asn Glu Trp Ser
    210                 215                 220

Thr Ser Ile Glu Asn Val Leu Lys Arg Tyr Gly Asn Ile Asn Ser Val
225                 230                 235                 240

Val Pro Gly His Gly Glu Val Gly Asp Lys Gly Leu Leu Leu His Thr
                245                 250                 255

Leu Asp Leu Leu Lys
            260

<210> SEQ ID NO 3
<211> LENGTH: 252
<212> TYPE: PRT
<213> ORGANISM: Bacillus cereus

<400> SEQUENCE: 3

Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Gln
            20                  25                  30

Ala Ser Lys Thr Glu Thr Gly Thr Ile Ser Ile Ser Gln Leu Asn Lys
        35                  40                  45

Asn Val Trp Val His Thr Glu Leu Gly Tyr Phe Asn Gly Glu Ala Val
    50                  55                  60

Pro Ser Asn Gly Leu Val Leu Asn Thr Ser Lys Gly Leu Val Leu Val
65                  70                  75                  80

Asp Ser Ser Trp Asp Asn Lys Leu Thr Lys Glu Leu Ile Glu Met Val
                85                  90                  95

Glu Lys Lys Phe Gln Lys Arg Val Thr Asp Val Ile Ile Thr His Ala
            100                 105                 110

His Ala Asp Arg Ile Gly Gly Ile Thr Ala Leu Lys Glu Arg Gly Ile
        115                 120                 125

Lys Ala His Ser Thr Ala Leu Thr Ala Glu Leu Ala Lys Asn Ser Gly
    130                 135                 140

Tyr Glu Glu Pro Leu Gly Asp Leu Gln Thr Ile Thr Ser Leu Lys Phe
145                 150                 155                 160

Gly Asn Thr Lys Val Glu Thr Phe Tyr Pro Gly Lys Gly His Thr Glu
                165                 170                 175

Asp Asn Ile Val Val Trp Leu Pro Gln Tyr Gln Ile Leu Ala Gly Gly
            180                 185                 190

Cys Leu Val Lys Ser Ala Glu Ala Lys Asp Leu Gly Asn Val Ala Asp
        195                 200                 205

Ala Tyr Val Asn Glu Trp Ser Thr Ser Ile Glu Asn Val Leu Lys Arg
    210                 215                 220

Tyr Gly Asn Ile Asn Ser Val Val Pro Gly His Gly Glu Val Gly Asp
225                 230                 235                 240

Lys Gly Leu Leu Leu His Thr Leu Asp Leu Leu Lys
                245                 250

<210> SEQ ID NO 4
<211> LENGTH: 774
<212> TYPE: DNA
<213> ORGANISM: Bacillus cereus

<400> SEQUENCE: 4
```

-continued

```
atgaaaaaga atacattatt aaaattaggg gtatgtgtta gtttactagg aataactcaa      60
tttgttagta caatttcttc tgtgaaagca gaacaaaagc tagagcaaat agtaatcaaa     120
aatgagacgg gaaccatttc aatatctcag ttaaacaaga atgtatgggt tcatacggag     180
ttaggttatt ttaatggaga agcagttcct tcgaacggtc tagttcttaa tacttctaaa     240
gggctagtac ttgttgattc ttcttgggat aacaaattaa cgaaggaact aatagaaatg     300
gtagaaaaga aatttcagaa gcgcgtaacg gatgtcatta ttacacatgc gcacgctgat     360
cgaattggcg gaataacagc gttgaaagaa agaggcatta aagcgcatag tacagcatta     420
accgcagaac tagcaaagaa cagtggatat gaagagccgc ttggagattt acaaacaatt     480
acgagtttaa agtttggcaa tacaaaagta gaaacgttct atccagggaa aggacataca     540
gaagataata ttgttgtttg gttgccacaa tatcaaattt tagctggagg ctgtttagta     600
aaatctgcgg aagctaaaga tttaggaaat gttgcggatg cgtatgtaaa tgaatggtct     660
acatcgattg agaatgtgct gaagcgatat ggaaatataa attcggtagt acctggtcat     720
ggagaagtag gagacaaggg attactttta catacattgg atttattaaa ataa           774
```

```

<210> SEQ ID NO 5
<211> LENGTH: 786
<212> TYPE: DNA
<213> ORGANISM: Bacillus cereus
<220> FEATURE:
<221> NAME/KEY: CDS
<222> LOCATION: (1)..(756)
<220> FEATURE:
<221> NAME/KEY: mat_peptide
<222> LOCATION: (94)..(756)

<400> SEQUENCE: 5 atg att caa aaa cga aag cgg aca gtt tcg ttc aga ctt gtg ctt atg       48
Met Ile Gln Lys Arg Lys Arg Thr Val Ser Phe Arg Leu Val Leu Met
    -30                 -25                 -20 tgc acg ctg tta ttt gtc agt ttg ccg att aca aaa aca tca gcg caa       96
Cys Thr Leu Leu Phe Val Ser Leu Pro Ile Thr Lys Thr Ser Ala Gln
-15                 -10                 -5                  -1  1 gct tcc gaa caa aag cta gag caa ata gta atc aaa aat gag acg gga      144
Ala Ser Glu Gln Lys Leu Glu Gln Ile Val Ile Lys Asn Glu Thr Gly
            5                   10                  15 acc att tca ata tct cag tta aac aag aat gta tgg gtt cat acg gag      192
Thr Ile Ser Ile Ser Gln Leu Asn Lys Asn Val Trp Val His Thr Glu
        20                  25                  30 tta ggt tat ttt aat gga gaa gca gtt cct tcg aac ggt cta gtt ctt      240
Leu Gly Tyr Phe Asn Gly Glu Ala Val Pro Ser Asn Gly Leu Val Leu
    35                  40                  45 aat act tct aaa ggg cta gta ctt gtt gat tct tct tgg gat aac aaa      288
Asn Thr Ser Lys Gly Leu Val Leu Val Asp Ser Ser Trp Asp Asn Lys
50                  55                  60                  65 tta acg aag gaa cta ata gaa atg gta gaa aag aaa ttt cag aag cgc      336
Leu Thr Lys Glu Leu Ile Glu Met Val Glu Lys Lys Phe Gln Lys Arg
                70                  75                  80 gta acg gat gtc att att aca cat gcg cac gct gat cga att ggc gga      384
Val Thr Asp Val Ile Ile Thr His Ala His Ala Asp Arg Ile Gly Gly
            85                  90                  95 ata aca gcg ttg aaa gaa aga ggc att aaa gcg cat agt aca gca tta      432
Ile Thr Ala Leu Lys Glu Arg Gly Ile Lys Ala His Ser Thr Ala Leu
        100                 105                 110 acc gca gaa cta gca aag aac agt gga tat gaa gag ccg ctt gga gat      480
Thr Ala Glu Leu Ala Lys Asn Ser Gly Tyr Glu Glu Pro Leu Gly Asp
    115                 120                 125
```

```
tta caa aca att acg agt tta aag ttt ggc aat aca aaa gta gaa acg      528
Leu Gln Thr Ile Thr Ser Leu Lys Phe Gly Asn Thr Lys Val Glu Thr
130             135                 140                 145 ttc tat cca ggg aaa gga cat aca gaa gat aat att gtt gtt tgg ttg      576
Phe Tyr Pro Gly Lys Gly His Thr Glu Asp Asn Ile Val Val Trp Leu
            150                 155                 160 cca caa tat caa att tta gct gga ggc tgt tta gta aaa tct gcg gaa      624
Pro Gln Tyr Gln Ile Leu Ala Gly Gly Cys Leu Val Lys Ser Ala Glu
        165                 170                 175 gct aaa gat tta gga aat gtt gcg gat gcg tat gta aat gaa tgg tct      672
Ala Lys Asp Leu Gly Asn Val Ala Asp Ala Tyr Val Asn Glu Trp Ser
    180                 185                 190 aca tcg att gag aat gtg ctg aag cga tat gga aat ata aat tcg gta      720
Thr Ser Ile Glu Asn Val Leu Lys Arg Tyr Gly Asn Ile Asn Ser Val
195                 200                 205 gta cct ggt cat gga gaa gta gga gac aag gga tta cttttacata           766
Val Pro Gly His Gly Glu Val Gly Asp Lys Gly Leu
210                 215                 220 cattggattt attaaaataa                                                786
```

<210> SEQ ID NO 6
<211> LENGTH: 252
<212> TYPE: PRT
<213> ORGANISM: Bacillus cereus

<400> SEQUENCE: 6

```

Val Pro Gly His Gly Glu Val Gly Asp Lys Gly Leu
210                 215                 220

<210> SEQ ID NO 7
<211> LENGTH: 759
<212> TYPE: DNA
<213> ORGANISM: Bacillus cereus

<400> SEQUENCE: 7

```
atgattcaaa aacgaaagcg acagtttcg ttcagacttg tgcttatgtg cacgctgtta      60
tttgtcagtt tgccgattac aaaaacatca gcgcaagctt ccaaaacaga cgggaacc     120
atttcaatat ctcagttaaa caagaatgta tgggttcata cggagttagg ttattttaat   180
ggagaagcag ttccttcgaa cggtctagtt cttaatactt ctaaagggct agtacttgtt   240
gattcttctt gggataacaa attaacgaag gaactaatag aaatggtaga aagaaattt    300
cagaagcgcg taacggatgt cattattaca catgcgcacg ctgatcgaat tggcggaata   360
acagcgttga agaaagagg cattaaagcg catagtacag cattaaccgc agaactagca    420
aagaacagtg atatgaaga gccgcttgga gatttacaaa caattacgag tttaaagttt    480
ggcaatacaa aagtagaaac gttctatcca gggaaaggac atacagaaga taatattgtt   540
gtttggttgc acaatatca aattttagct ggaggctgtt tagtaaaatc tgcggaagct    600
aaagatttag gaaatgttgc ggatgcgtat gtaaatgaat ggtctacatc gattgagaat   660
gtgctgaagc gatatggaaa tataaattcg gtagtacctg gtcatggaga agtaggagac   720
aagggattac ttttacatac attggattta ttaaaataa                          759
```

<210> SEQ ID NO 8
<211> LENGTH: 4
<212> TYPE: PRT
<213> ORGANISM: Bacillus cereus

<400> SEQUENCE: 8

Val Met Lys Asn
1

<210> SEQ ID NO 9
<211> LENGTH: 23
<212> TYPE: PRT
<213> ORGANISM: Bacillus cereus

<400> SEQUENCE: 9

Glu Gln Lys Leu Glu Gln Ile Val Ile Lys Asn Glu Thr Gly Thr Ile
1               5                   10                  15

Ser Ile Ser Gln Leu Asn Lys
            20

<210> SEQ ID NO 10
<211> LENGTH: 23
<212> TYPE: PRT
<213> ORGANISM: Bacillus weihenstephanensis

<400> SEQUENCE: 10

Glu Gln Lys Leu Glu Gln Lys Val Ile Lys Asn Glu Thr Gly Thr Ile
1               5                   10                  15

Ser Ile Ser Gln Leu Asn Lys
            20

<210> SEQ ID NO 11
<211> LENGTH: 23
<212> TYPE: PRT

<213> ORGANISM: Bacillus sp.

<400> SEQUENCE: 11

Ser Gln Lys Val Glu Gln Ile Val Lys Asn Glu Thr Gly Thr Ile
1               5                   10                  15
Ser Ile Ser Gln Leu Asn Lys
            20

<210> SEQ ID NO 12
<211> LENGTH: 23
<212> TYPE: PRT
<213> ORGANISM: Bacillus cereus

<400> SEQUENCE: 12

Glu Gln Lys Leu Glu Gln Lys Val Ile Lys Asn Glu Ala Gly Thr Ile
1               5                   10                  15
Ser Ile Ser Gln Leu Asn Lys
            20

<210> SEQ ID NO 13
<211> LENGTH: 23
<212> TYPE: PRT
<213> ORGANISM: Bacillus cereus

<400> SEQUENCE: 13

Ser Gln Lys Val Glu Lys Thr Val Ile Lys Asn Glu Thr Gly Thr Ile
1               5                   10                  15
Ser Ile Ser Gln Leu Asn Lys
            20

<210> SEQ ID NO 14
<211> LENGTH: 23
<212> TYPE: PRT
<213> ORGANISM: Bacillus cereus

<400> SEQUENCE: 14

Ser Gln Lys Val Glu Lys Thr Val Ile Lys Asn Glu Thr Gly Thr Ile
1               5                   10                  15
Ser Ile Ser Gln Leu Asn Lys
            20

<210> SEQ ID NO 15
<211> LENGTH: 23
<212> TYPE: PRT
<213> ORGANISM: Bacillus anthracis

<400> SEQUENCE: 15

Glu Arg Lys Val Glu His Lys Val Ile Lys Asn Glu Thr Gly Thr Ile
1               5                   10                  15
Ser Ile Ser Gln Leu Asn Lys
            20

<210> SEQ ID NO 16
<211> LENGTH: 23
<212> TYPE: PRT
<213> ORGANISM: Bacillus anthracis

<400> SEQUENCE: 16

Glu Arg Lys Val Glu His Lys Val Ile Lys Asn Glu Thr Gly Thr Ile
1               5                   10                  15
Ser Ile Ser Gln Leu Asn Lys
            20

```
<210> SEQ ID NO 17
<211> LENGTH: 23
<212> TYPE: PRT
<213> ORGANISM: Bacillus cereus

<400> SEQUENCE: 17

Ser Gln Lys Val Glu Gln Lys Val Met Lys Asn Glu Ala Gly Thr Ile
1               5                   10                  15

Ser Ile Ser Gln Leu Asn Lys
            20

<210> SEQ ID NO 18
<211> LENGTH: 23
<212> TYPE: PRT
<213> ORGANISM: Bacillus cereus

<400> SEQUENCE: 18

Glu Arg Thr Val Glu His Lys Val Ile Lys Asn Glu Thr Gly Thr Ile
1               5                   10                  15

Ser Ile Ser Gln

-continued

```
<220> FEATURE:
<223> OTHER INFORMATION: PCR primer

<400> SEQUENCE: 23
aggaaatgtt gcggatgc 18

<210> SEQ ID NO 24
<211> LENGTH: 21
<212> TYPE: DNA
<213> ORGANISM: Artificial sequence
<220> FEATURE:
<223> OTHER INFORMATION: PCR primer
<400> SEQUENCE: 24
ccttcgttaa tttgttatcc c 21

<210> SEQ ID NO 25
<211> LENGTH: 4
<212> TYPE: PRT
<213> ORGANISM: Bacillus cereus

<400> SEQUENCE: 25

Val Ile Lys Asn
1

<210> SEQ ID NO 26
<211> LENGTH: 39
<212> TYPE: DNA
<213> ORGANISM: Artificial sequence
<220> FEATURE:
<223> OTHER INFORMATION: PCR primer
<400> SEQUENCE: 26
cgcgaagctt ccgaacaaaa gctagagcaa atagtaatc 39

<210> SEQ ID NO 27
<211> LENGTH: 47
<212> TYPE: DNA
<213> ORGANISM: Artificial sequence
<220> FEATURE:
<223> OTHER INFORMATION: PCR primer
<400> SEQUENCE: 27
gccgaagctt ttattttaat aaatccaatg tatgtaaaag taatccc 47

<210> SEQ ID NO 28
<211> LENGTH: 19
<212> TYPE: PRT
<213> ORGANISM: Bacillus cereus

<400> SEQUENCE: 28

Gln Ala Ser Glu Gln Lys Leu Glu Gln Ile Val Ile Lys Asn Glu Thr
1 5 10 15

Gly Thr Ile

<210> SEQ ID NO 29
<211> LENGTH: 10
<212> TYPE: PRT
<213> ORGANISM: Bacillus cereus

<400> SEQUENCE: 29

Ile Val Ile Lys Asn Glu Thr Gly Thr Ile
1 5 10

<210> SEQ ID NO 30

```
<211> LENGTH: 6
<212> TYPE: PRT
<213> ORGANISM: Bacillus cereus

<400> SEQUENCE: 30

Asn Glu Thr Gly Thr Ile
1               5

<210> SEQ ID NO 31
<211> LENGTH: 5
<212> TYPE: PRT
<213> ORGANISM: Bacillus cereus

<400> SEQUENCE: 31

Glu Thr Gly Thr Ile
1               5

<210> SEQ ID NO 32
<211> LENGTH: 11
<212> TYPE: PRT
<213> ORGANISM: Bacillus cereus

<400> SEQUENCE: 32

Glu Gln Lys Leu Glu Gln Ile Val Ile Lys Asn
1               5                   10

<210> SEQ ID NO 33
<211> LENGTH: 9
<212> TYPE: PRT
<213> ORGANISM: Bacillus cereus

<400> SEQUENCE: 33

Glu Thr Gly Thr Ile Ser Ile Ser Gln
1               5

<210> SEQ ID NO 34
<211> LENGTH: 11
<212> TYPE: PRT
<213> ORGANISM: Bacillus cereus

<400> SEQUENCE: 34

Gly Leu Leu Leu His Thr Leu Asp Leu Leu Lys
1               5                   10

<210> SEQ ID NO 35
<211> LENGTH: 10
<212> TYPE: PRT
<213> ORGANISM: Bacillus cereus

<400> SEQUENCE: 35

Gln Ala Ser Glu Thr Gly Thr Ile Ser Ile
1               5                   10

<210> SEQ ID NO 36
<211> LENGTH: 8
<212> TYPE: PRT
<213> ORGANISM: Bacillus cereus

<400> SEQUENCE: 36

Ser Glu Thr Gly Thr Ile Ser Ile
1               5

<210> SEQ ID NO 37
<211> LENGTH: 11
<212> TYPE: PRT
<213> ORGANISM: Bacillus cereus
```

```
<400> SEQUENCE: 37

Glu Gln Lys Leu Glu Gln Ile Val Ile Lys Asn
1               5                   10

<210> SEQ ID NO 38
<211> LENGTH: 12
<212> TYPE: PRT
<213> ORGANISM: Bacillus cereus

<400> SEQUENCE: 38

Gln Ala Ser Lys Thr Glu Thr Gly Thr Ile Ser Ile
1               5                   10

<210> SEQ ID NO 39
<211> LENGTH: 7
<212> TYPE: PRT
<213> ORGANISM: Bacillus cereus

<400> SEQUENCE: 39

Glu Thr Gly Thr Ile Ser Ile
1               5

<210> SEQ ID NO 40
<211> LENGTH: 5
<212> TYPE: PRT
<213> ORGANISM: Bacillus cereus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 40

Asn Xaa His Xaa Asp
1               5

<210> SEQ ID NO 41
<211> LENGTH: 5
<212> TYPE: PRT
<213> ORGANISM: Bacillus cereus

<400> SEQUENCE: 41

Ile Val Ile Lys Asn
1               5
```